United States Patent
Mallapragada et al.

(10) Patent No.: US 7,183,369 B1
(45) Date of Patent: Feb. 27, 2007

(54) INJECTIBLE BODILY PROSTHETICS EMPLOYING METHACRYLIC COPOLYMER GELS

(75) Inventors: Surya K. Mallapragada, Ames, IA (US); Brian C. Anderson, Lake Bluff, IL (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 10/367,414

(22) Filed: Feb. 14, 2003

(51) Int. Cl.
  *C08F 116/16* (2006.01)
(52) U.S. Cl. .................... 526/333; 526/277; 526/279; 526/310; 526/317.1; 526/328.5; 526/332
(58) Field of Classification Search ............... 526/277, 526/279, 310, 317.1, 328.5, 332, 333
See application file for complete search history.

(56) References Cited

OTHER PUBLICATIONS

Lee et al. Macromolecules, 35(22), 8540-5881, 2002.*
Deshpandhe et al. J. controlled Release, 81(1-2), 185-199, 2002.*
Even et al. Polymeric Materials Science and Engineering, 84, 955-956, 2001.*
Vamvakaki et al. Macromolecules, 32(6), 2088-2090, 1999.*
Anderson et al. Mat. res. Soc. symp. Proc., 662, NNi.8/1-NN1.8/6, 2001.*

* cited by examiner

*Primary Examiner*—Helen L. Pezzuto
(74) *Attorney, Agent, or Firm*—Quarles & Brady LLP

(57) ABSTRACT

The present invention provides novel block copolymers as structural supplements for injectible bodily prosthetics employed in medical or cosmetic procedures. The invention also includes the use of such block copolymers as nucleus pulposus replacement materials for the treatment of degenerative disc disorders and spinal injuries. The copolymers are constructed by polymerization of a tertiary amine methacrylate with either a (poly(ethylene oxide)-b-poly(propylene oxide)-b-poly(ethylene oxide) polymer, such as the commercially available Pluronic® polymers, or a poly(ethylene glycol) methyl ether polymer.

39 Claims, 10 Drawing Sheets

INJECTIBLE BODILY PROSTHETICS EMPLOYING METHACRYLIC COPOLYMER GELS

STATEMENT REGARDING FEDERALLY SPONSORED RESEARCH OR DEVELOPMENT

The present invention was developed using financial support provided by the U.S. Department of Energy under contract number W-7405-ENG-82. The United States Government has certain rights in the present invention.

CROSS-REFERENCE TO RELATED APPLICATIONS

None.

BACKGROUND OF THE INVENTION

The present invention generally relates to copolymers that serve as structural supplements in injectible bodily prosthetics employed in medical or cosmetic procedures. The present invention further relates to injectible polymeric nucleus pulposus replacement materials, and the use of such materials in treating degenerative intervertebral disc disorders and spinal injuries.

The intervertebral disc is a complex joint anatomically and functionally. It is composed of three component structures: the nucleus pulposus, the annulus fibrosus and two vertebral end-plates. The nucleus pulposus is a generally loose or amorphous hydrogel which serves to support the load applied to the disc, and is mainly responsible for the compressive properties of the disc. The annulus fibrosus forms the outer limiting boundary of the disc, and serves to maintain the nucleus pulposus in compression while inhibiting over-rotation of the disc. The vertebral end-plates are composed of hyaline cartilage, and separates the disc from the adjacent vertebral bodies. This layer acts as a transitional zone between the hard, bony vertebral bodies and the soft disc.

Damage or displacement to the intervertebral disc may be caused by trauma, disease, or an inherent disorder. In these cases, the nucleus pulposus may herniate and/or protrude into the vertebral canal or intervertebral foramen, resulting in back pain and/or loss of mechanical spinal function.

Current treatment options include conservative bed rest, a laminectomy (removal of the disc), as well as highly invasive surgical procedures, such as spinal fusion. Although these treatments offer pain relief, they do not restore the mechanical function of the spine. Other options involve replacing the damaged or degenerated disc with a synthetic disc implant, such as Charite. Unfortunately, such disc replacements often lead to stress shielding and other deleterious effects, as well as highly invasive surgery.

Nucleus pulposus replacement is one possible treatment for disc injuries and other degenerative disc disorders. Nucleus pulposus replacement typically involves the replacement of the damaged pulposus with a prosthetic nucleus pulposus. For example, U.S. Pat. No. 5,047,055 to Bao et al., which is incorporated herein by reference, describes the use of a hydrogel prosthetic nucleus as a treatment for disc injuries and other degenerative disc disorders. The hydrogel is prepared by cast molding or lathecutting, and then implanted in conjunction with a laminectomy operation, such as discectomy or microdiscectomy, percutaneous discectomy, or chemonucleolysis. All of which require an invasive surgery.

What is needed is a new hydrogel replacement system that is less invasive.

BRIEF SUMMARY OF THE INVENTION

The present invention provides novel copolymers as structural supplements for injectible bodily prosthetics employed in medical or cosmetic procedures. The invention also includes the use of such copolymers as nucleus pulposus replacement materials for the treatment of degenerative disc disorders and spinal injuries. The block copolymers are described in detail below and are prepared through polymerization of a tertiary amine methacrylate with either a polyethylene glycol methyl ether, or a poly(ethylene oxide)-b-poly (propylene oxide)-b-poly(ethylene oxide).

The block copolymers exhibit cationic pH-sensitive behavior and good water solubility. At concentrations and temperatures greater than about 15% by weight tertiary amine methacrylate and 35° C., respectively, aqueous solutions including the present copolymers undergo a sol-gel transition to form non-crosslinked gels. Preferably, the copolymers are at a concentration of greater than 25%, and more preferably greater than 30%, and most preferably greater than 35% by weight tertiary amine methacrylate. The gels are non-cytotoxic and possess structural properties which allow their use as an injectible structural supplement in certain medical treatments, such as spinal injuries and degenerative disc disorders, or other medical or cosmetic procedures requiring the introduction of a gelatinous material.

The treatment of degenerative disc disorders and spinal injuries is accomplished by injecting an aqueous solution including the copolymers into the appropriate locations between the vertebrae. Upon raising the temperature of the solution to body temperatures (i.e., 37° C.), and upon placing the solution at neutral pH, copolymers with concentrations of greater than 17% by weight tertiary amine methacrylate will form a gel having structural characteristics capable of providing a cushioning effect between the vertebrae. Preferably, the copolymer injection will have a concentration of greater than 25%, and more preferably greater than 30%, and most preferably greater than 35% by weight tertiary amine methacrylate. For long term applications, the gels may be further stabilized by injecting a basic solution along with the aqueous copolymer solution to cause the copolymers to further assemble into a gel having stronger structural characteristics. In addition, or in the alternative, a suitable cross-linking agent, such as a diacid, may be injected with the aqueous copolymer solution to form crosslinked gels, also having stronger structural characteristics. Treatments for other medical or cosmetic applications may be performed using the same procedure.

One advantage of the present invention is that the provided copolymers form thermoreversible gels that, when at room temperature or lower, may be injected into the desired location while being in an aqueous solution. Upon being exposed to the body's temperature (i.e., 37° C.), the copolymers will instantly form a gel providing the desired structural support.

A second advantage of the present invention is that the copolymers may include groups on their side chains so as to allow the copolymers to be chemically cross-linked to each other, thus providing additional stability for long term applications.

These and other advantages and features of the present invention will become apparent after review of the specification, drawings, and claims.

BRIEF DESCRIPTION OF THE SEVERAL VIEWS OF THE DRAWINGS

FIG. 2A depicts a reaction in THF solvent between DEAEM monomer and Pluronic® F127 initiator to form a living polymer. FIG. 2B depicts termination of the living polymer with methanol. FIG. 2C depicts termination of the living polymer with benzyl bromide.

DETAILED DESCRIPTION OF THE INVENTION

The present invention provides novel copolymers for use as structural supplements in injectable bodily prosthetics. The present invention also includes the use of such copolymers as nucleus pulposus replacement materials for the treatment of degenerative disc disorders and spinal injuries. The copolymers exhibit cationic pH-sensitive behavior, good water solubility, and thermoreversible gelation characteristics. The novel compounds are represented by the following formula (I):

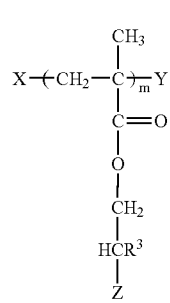
(I)

wherein X is represented by the formula:

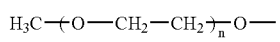
(a)

in which n is an integer in the range of 30 to 20,000, or

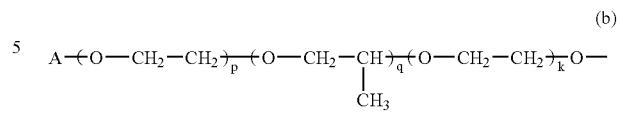
(b)

in which p is an integer in the range of 30 to 20,000, q is an integer in the range of 0 to 20,000, and k is an integer in the range of 0 to 20,000, and A is represented by the formula:

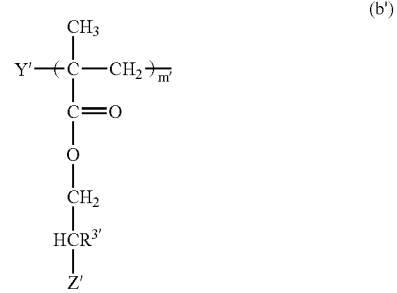
(b')

in which m' is a number in the range of 0 to 5,000;

Y is represented by the formula:

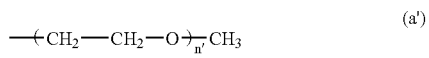
(a')

in which n' is in the range of 30 to 20,000, or if group X is (b), then Y is either represented by the formula (a'), formula (b), or a terminator group, and Y' is either represented by formula (a'), formula (b), or a terminator group;

m is a number in the range of 1 to 5,000.

$R^3$ and $R^{3'}$ are either a hydrogen or a $C_{1-6}$ alkyl group; and

Z and Z' are selected from the group of $NR^6R^7$, $P(OR^8)_3$, $SR^9$, SH,

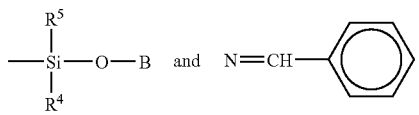

in which $R^6$, $R^7$, and $R^8$ are the same or different $C_{1-6}$ alkyl groups or $R^6$ or $R^7$ are hydrogen when Z is a protected group, $R^9$ is a tri($C_{1-6}$ alkyl)silyl group, and B is a $C_{1-6}$ alkyl group.

Figure 1:
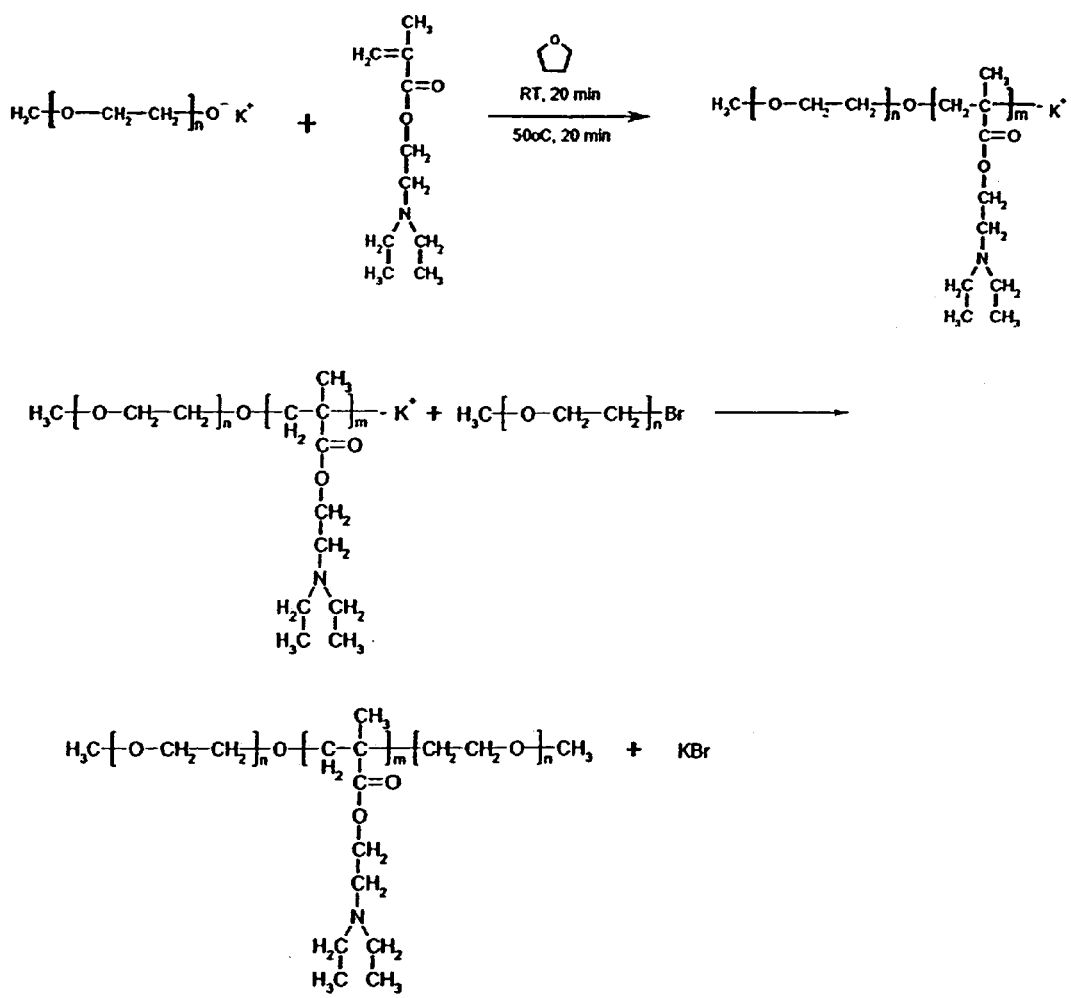
FIG. 1 is an illustration of the reaction scheme for the triblock copolymer.
Figure 2:
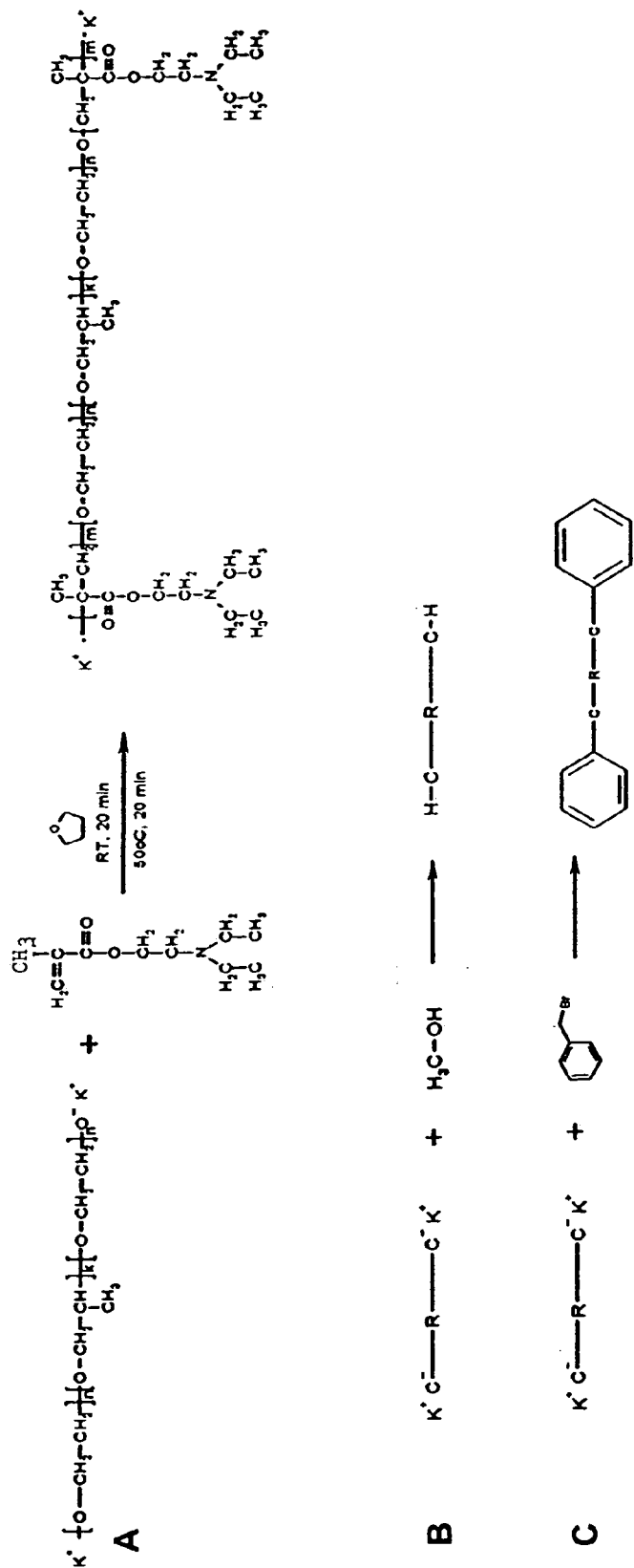
FIG. 2 is an illustration of the reaction scheme for pentablock polymerization.

As illustrated in FIGS. 1 and 2, the copolymers may be synthesized by anionic polymerization of a tertiary amine methacrylate having the following formula (II):

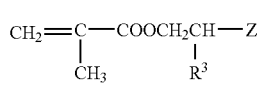
(II)

wherein $R^3$ and Z are as defined for formula (I). The tertiary amine methacrylate may also include low molecular weight or high molecular weight varieties of said compounds. Preferably $R^3$ is a hydrogen. In the most preferred embodiment, the tertiary amine methacrylate is 2-(N,N-diethylaminoethyl methacrylate).

The X group in formula (I) may be generally derived from a polyethylene glycol methyl ether, or a poly(ethylene oxide)-b-poly(propylene oxide)-b-poly(ethylene oxide), such as the commercially available Pluronic® triblock copolymer, or any low molecular weight or high molecular weight varieties of said compounds. The X group is preferably represented by either (a) or (b) of formula (I) above, and may be either substituted or unsubstituted.

The reaction for preparing the copolymers is generally set forth in FIGS. 1–4. The copolymers of the present invention are preferably synthesized using anionic polymerization, but may also be prepared using any technique that results in the synthesis of compounds having the above described formula (I). One such method is described by Nagasaki et al. in European Patent No. EP 0976767A1, which is incorporated herein by reference.

In the preferred embodiment, the copolymers of the present invention are prepared by first reacting a polymerization macroinitiator (based on either (a) or (b) of Group X in formula (I)) with a monomer. The reaction may be conducted according to any method known in the art, and will depend primarily on the compounds utilized. The combination of the polymerization macroinitiator and an alkali metal provides a polymerization macroinitiator that can be represented by the following formula (III):

Q—M    (III)

wherein Q is the monomer providing (a) or (b) of Group X, which initiates a living polymerization including either (a) or (b) of Group X, and M is an alkali metal, such as sodium or potassium. When Q is represented by (b) of Group X, the alkali metal M will also represent A of group (b) to allow polymerization to occur on both ends of group (b). This macroinitiator is then reacted with the tertiary amine methacrylate of formula (II) to provide living copolymers as illustrated in FIGS. 1 and 2.

In the case where Group X is represented by (a), a macroterminator may be prepared to terminate the oxyanionic polymerization of the monomer providing (a') for Group Y. In the preferred embodiment, the macroterminator may be represented by the following formula (IV):

Figure 4:
FIG. 4 is an illustration of the reaction scheme for the formation of one macroterminator which may be used in the triblock polymerization.

Q'—M'    (IV)

wherein Q' is the monomer providing (a') of Group Y, and M' is a bromide, as illustrated in FIG. 4. This brominated compound is then reacted with the living copolymer to provide a triblock copolymer as represented by formula (I), and as illustrated in FIG. 1.

In the case where Group X is represented by (b), the living copolymers are reacted after their construction with an appropriate compound to terminate further polymerization. Generally, when group X of formula (I) is (b), the termination will cause Y and/or Y' of formula (I) to be a terminator group. The terminator group may be either a reactive or nonreactive terminator group, and may be either protected or unprotected depending on the nature of the terminator employed and the intended use of the copolymer. Such terminator groups are well known in the art. Examples of such terminator groups include, without limitation, alkyl groups, carboxylic groups, COOH, $CH_2$—Ph, hydrogen, $CH_3$ or benzene.

The polymerization reaction may be carried out with or without the presence of an inert solvent, but preferably includes the use of an inert solvent. As used herein, the term "inert solvent" means any solvent that neither reacts with nor exerts an adverse influence on the polymerization reaction or the initiator and the formed polymer. Examples of such solvents include liquid solvents that do not react with alkali metal alcoholates under reaction conditions, including ether solvents, such as tetrahydrofuran, dioxane, diethyl ether and dimethoxyethane; aprotic solvents such as dimethyl sulfoxide, N,N-dimethylformamide, N,N-dimethylacetamide, and hexamethylphosphoric triamide; aliphatic hydrocarbons such as pentane, hexane and cyclohexane; and aromatic hydrocarbons such as benzene, toluene and xylene, with ethers such as tetrahydrofuran most preferred.

The amount of inert solvent employed, if any, will generally determine the speed at which the reaction will occur. In general, the reaction will be slower as the relative amount of the solvent increase. Therefore, the solvent is preferably used in an amount of 0.01 to 1,000 parts by volume of solvent to volume of monomer, and more preferably 0.5 to 100 parts by volume of solvent to volume of monomer.

The ratio of n and n' to m, and p, q and k to m and m', in formula (I) will be generally controlled by the molar ratio of Q and Q' of formula (III) and formula (IV) to the compound of formula (II). In general, Q may be used in a molar ratio of 0.0001 to 100 moles per mole of the formula (II) compound, and more preferably 0.0001 mole to 1 mole per mole of the formula (II) compound.

The block copolymers maintain the properties of thermoreversible gelation as well as thermally induced micellization in aqueous solutions. Under the appropriate concentration and thermal conditions, aqueous solutions including the present copolymers will undergo a sol-gel transition to form non-crosslinked gels. Such transitions will generally occur when the concentrations by weight of the tertiary amine methacrylate of formula (II) is greater than 17%, and preferably greater than 25%, and more preferably greater than 30%, and most preferably greater than 35%, and when the temperature of the solution exceeds 35° C. at neutral pH. Interestingly, at temperatures of about 70° C. to 80° C. and at basic pH (pH of greater than 10), the copolymers will also form blobs completely by self assembly.

The copolymers of the present invention include additional features that provide several advantages over existing technologies. For example, the use of DEAEM in the preferred embodiment increases the binding affinity of the copolymers so as to cause the copolymers to experience advanced cohesion, thus improving the mechanical properties (stiffness, etc.) of the gel as compared to other similar gels, such as Pluronics®. In addition, some copolymers may be prepared to include amine or carboxylic endcaps. These end caps, in turn, enable the copolymers to be chemically cross-linked using compounds such as diacids or diamines as is well known in the art. Moreover, diacids (or anhydride versions of the diacids) can be used to crosslink copolymers if they contain primary or secondary amines. The crosslinking of the copolymers can thus provide additional stability for long term applications. The copolymers are also non-cytotoxic when introduced into living tissues.

The mechanical properties of the gels allow for their use as structural supplements for injectible bodily prosthetics to used in certain medical treatments, such as treatments for spinal injuries and degenerative disc disorders, or other medical or cosmetic procedures requiring the introduction of a gelatinous material. As used herein, the term "injectible bodily prosthetic" is intended to mean a synthetic composition that replaces a bodily part removed or missing from the body of the patient. The prosthetic may be in the form of the copolymers of the present invention injected into and replacing the removed or missing bodily part, or the copolymers in association with a secondary component, such as a diacid, that causes the formation of cross-linking gels from the copolymers, or the copolymers injected into a membrane structure intended to encapsulate the copolymer gel while placed in the desired body location. Such membrane structures are well known and readily available in the art.

The treatment of degenerative disc disorders and spinal injuries may be achieved by injecting the copolymers while in an aqueous solution into the appropriate locations between the vertebrae. Upon raising the temperature of the solution to body temperatures (i.e., 37° C.), and upon placing the solution at neutral pH, copolymers with concentrations of greater than 17% by weight tertiary amine methacrylate will form a gel having structural characteristics capable of providing a cushioning effect between the vertebrae. Preferably, the copolymer injection will have a concentration of greater than 25%, and more preferably greater than 30%, and most preferably greater than 35% by weight tertiary amine methacrylate.

For long term applications, the gels may be further stabilized by injecting a basic solution along with the aqueous copolymer solution to cause the copolymers to further assemble into a gel having stronger structural characteristics. In addition, or in the alternative, a suitable cross-linking agent, such as a diacid, may be injected with the aqueous copolymer solution to form cross-linked gels having stronger structural characteristics. Such basic solutions and cross-linking agents are commonly known in the art.

Treatments for other medical or cosmetic applications may be performed using the same procedure. For example, the copolymers of the present invention may find use as structural supplements in cosmetic procedures intended to enhance certain body parts (i.e., cheeks, breasts, buttocks, etc). In such cases, the copolymers may be injected into a bodily prosthetic including a membrane structure intended to encapsulate the copolymer gel while placed in the desired body location. Similarly, the copolymers may be used to replace damaged cartilage in areas such as the knee cap, or other areas susceptible to injury. The copolymers may also find use in medical applications intended to alleviate discomfort in bodily joints caused by disorders such as rheumatoid arthritis or osteoporosis. In this case, the copolymers would be injected into the joint area to provide the desired relief.

The present invention is more specifically explained with reference to the following non-limiting examples, which are intended to illustrate the invention and are not to be construed as to limit the scope of the invention.

EXAMPLES

Example 1

PEG-b-PDEAEM-b-PEG Triblock Copolymer

FIG. 1 illustrates the reaction scheme for preparing a triblock copolymer having the following formula (I-a):

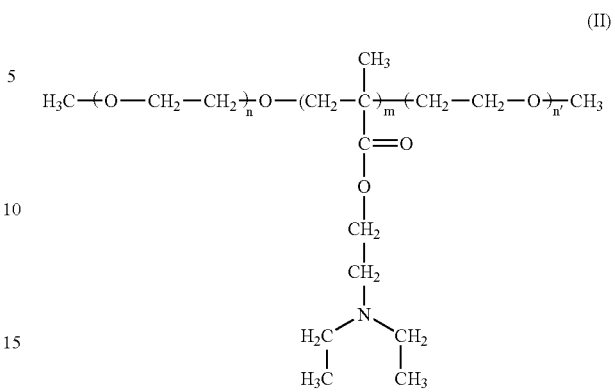

The above triblock copolymer (I-a) was prepared using N,N-(diethyl amino)ethyl methacrylate (DEAEM) (Sigma-Aldrich, St. Louis, Mo.) as the monomer, poly(ethylene glycol) methyl ether (PEGME) ($\overline{M}_n$~5000, Polysciences Inc., Warrington, Pa.) as the X, with a potassium salt of PEGME as the X group macroinitiator and PEGMEBr as the Y group macroterminator, and tetrahydrofuran (THF) (Sigma-Aldrich Co., St. Louis Mo.) as the solvent. The DEAEM was dried over calcium hydride and purified by distillation under reduced pressure. The PEGME was dried by heating under vacuum. The THF was dried by passing through solvent purification columns of alumina and Q5 copper/silica/alumina catalyst (columns, Solv-Tek, Berryville, Va.; Q5, Engelhard Corp, Iselin, N.J.). All flasks and magnetic stir bars used were either flame dried and cooled under an inert atmosphere or heated overnight at 180° C. and cooled under an inert atmosphere.

To prepare the first polymerization macroinitiator, the potassium hydride, stored under mineral oil, was first washed with THF in an inert atmosphere in a round bottom flask (enough dry THF was added to completely submerse the solid potassium hydride). PEGME was also dissolved in THF in a round bottom flask by heating the THF and PEGME to slightly above room temperature. The solvated polymer was then transferred via canulla into a flask containing the potassium hydride to form the alcoholate as illustrated in FIG. 1.

An appropriate amount of DEAEM was then added via air-free syringe or canulla to the alcoholate solution above while stirring at 400 rpm at room temperature for 20 min, followed by 50° C. for 20 minutes, resulting in the formation of a living PEGME-b-PDEAEM polymers. These living polymers were then terminated with a previously prepared macroterminator of brominated poly(ethylene glycol) methyl ether, thus providing the above triblock copolymer.

The macroterminator was previously prepared by reacting PEGME with phosphorous tribromide as illustrated in FIG. 4. The PEGME was initially dissolved in THF in a round bottom flask by heating the THF and PEGME to slightly above room temperature. The solvated polymer was then transferred via canulla into a flask containing the phosphorous tribromide while stirring, followed by 50° C. overnight, to obtain the brominated poly(ethylene glycol)methyl ether.

Figure 5:
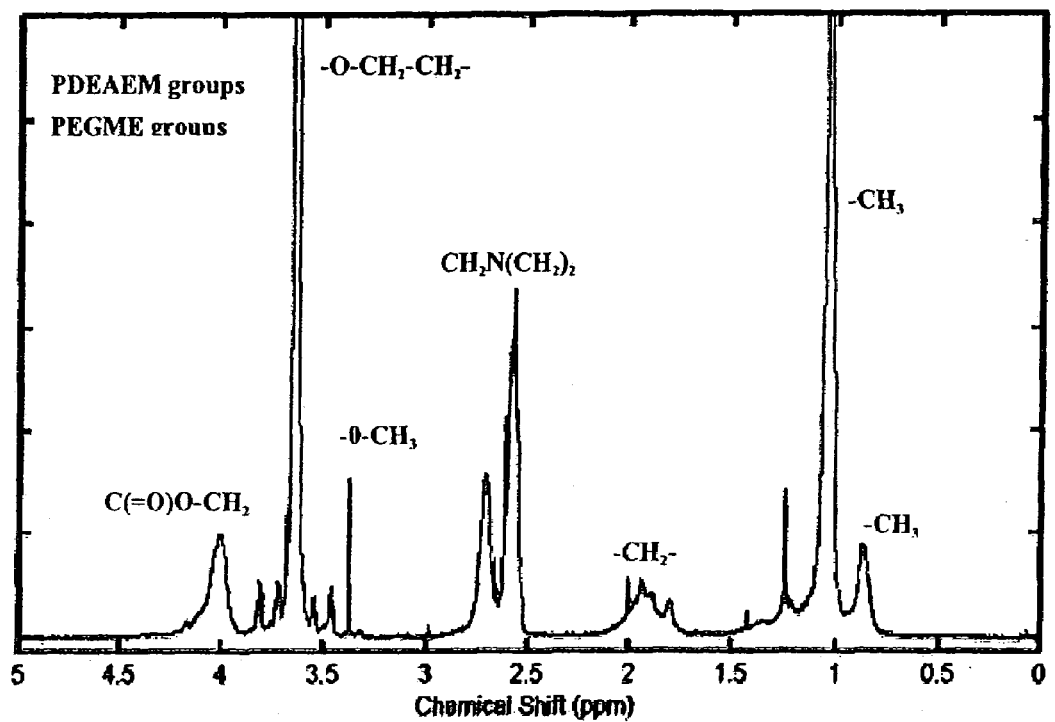
FIG. 5 is an $^1$H NMR analysis of PEGME-b-PDEAEM-b-PEGME triblock copolymer.

The resulting triblock copolymers were precipitated in −78° C. n-hexane and dried under vacuum for at least 24 hours. The polymer was then characterized and its pH sensitivity tested. FIG. 5 depicts an $^1$H NMR analysis of PEGME-b-PDEAEM-b-PEGME triblock copolymer.

Example 2

PDEAEM-b-PEO-b-PPO-b-PEO-b-PDEAEM Pentablock Copolymer

FIG. 2 illustrates the reaction scheme for preparing a pentablock copolymer having the following formula (I-b):

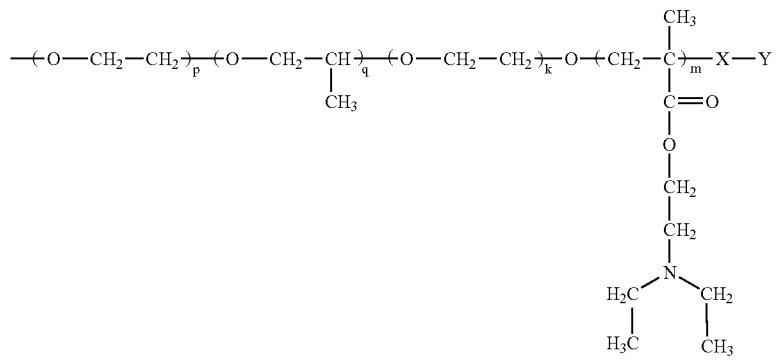

The above pentablock copolymer (I-b) was prepared using N,N-(diethyl amino)ethyl methacrylate (DEAEM) as the monomer, disubstituted potassium salt of poly(ethylene oxide)-b-poly(propylene oxide)-b-poly(ethylene oxide) (Pluronic™ F127, $\overline{M}_n$=12,600, 70% w/w PEG) (Sigma-Aldrich Co St. Louis, Mo.) as the polymerization initiator, and tetrahydrofuran (THF) as the solvent. The DEAEM and THF were dried as in Example 1 above. The Pluronic® was dried by heating under vacuum.

Figure 3:
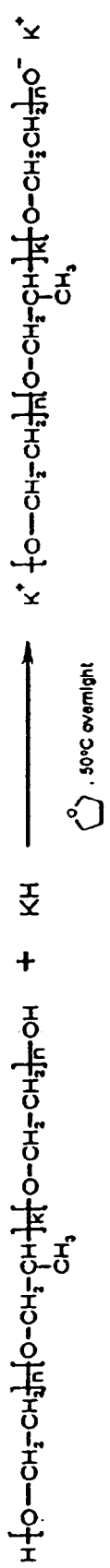
FIG. 3 is an illustration of the reaction scheme for pentablock polymerization initiator formation.

To prepare the polymerization initiator illustrated in FIG. 3, the potassium hydride, stored under mineral oil, was first washed with THF in an inert atmosphere in a round bottom flask as in Example 1. The Pluronic was then dissolved in THF in a round bottom flask by heating the THF and Pluronic to slightly above room temperature. The solvated polymer was the transferred via canulla into a flask containing the potassium hydride to form the alcoholate.

An appropriate amount of DEAEM was added via air-free syringe or canulla to the alcoholate polymerization initiator while stirring at 400 rpm at room temperature for 20 min, followed by 50° C. for 20 minutes. The living polymers were then terminated with an injection of methanol or benzyl bromide. The resulting polymers were precipitated in −78° C. n-hexane and dried under vacuum for at least 24 hours. The polymer was then characterized and its pH sensitivity tested.

Example 3

Characterization and pH Sensitivity Testing

Nuclear Magnetic Resonance and Gel Permeation Chromatography

The pentablock copolymers from Example 2 above were tested to measure their pH sensitivity and to determine their physical characteristics. NMR data was collected on Varian VXR400 (400 MHz) and Varian VXR300 (300 MHz) spectrometers. Chloroform-d was used as the solvent for most samples. For samples in which phenyl protons were used as a functionality marker, acetone-$d_6$ was used to avoid peak overlap.

Differential scanning calorimetry (DSC) was used to evaluate two thermodynamic properties of the pentablock materials. First, the onset of the micellization temperature, $T_m$, was determined as reported by Anderson et al. *J. Pharm. Sci.*, 91:180 (2002). Second, the endothermic enthalpy ($\Delta H$) of the micellization phase transition was measured by integrating the micellization peak.

All the samples prepared showed PDI values similar to the polymerization initiators used, indicating very little added polydispersity due to the PDEAEM blocks (Table 1). The apparent slight decrease in PDI from the polymerization initiator (sample H) to the block copolymers was assumed to be due to a higher reactivity of the lower molecular weight initiators relative to the higher molecular weight initiators, as well as the bimodal nature of the Pluronic® copolymer. For Pluronic® F127, the lower molecular weight mode was on the order of $\overline{M}_p$=6000 g/mol, whereas the upper mode had an $\overline{M}_p$ of approximately 14,000 g/mol. The distance between the modes appeared to get smaller as DEAEM was added to the polymers, resulting in a slightly lower PDI. As appears to be the case in other studies with PDEAEM, GPC was not always an accurate measure of $\overline{M}_n$ or $\overline{M}_w$, most likely due to the binding of the DEAEM moiety with the column packing and the high molecular weight of the DEAEM pendent groups.

TABLE 1

Sample polymerizations of F127-initiated pentablock copolymers.

| Sample ID | Initiator | Target $\overline{M}_n$ | $\overline{M}_n$ (NMR) | PDI (GPC) | DEAEM % |
|---|---|---|---|---|---|
| A | F127 | 19810 | 19730 | 1.20 | 36.2% |
| B | F127 | 16930 | 15670 | 1.19 | 19.6% |
| C | F127 | 15600 | 13890 | 1.19 | 9.3% |
| D | F127 | 14530 | 13330 | 1.18 | 5.4% |
| E | F127 | 13930 | 12840 | 1.20 | 1.9% |
| H | F127 | — | 12600 | 1.23 | 0% |

Figure 6:
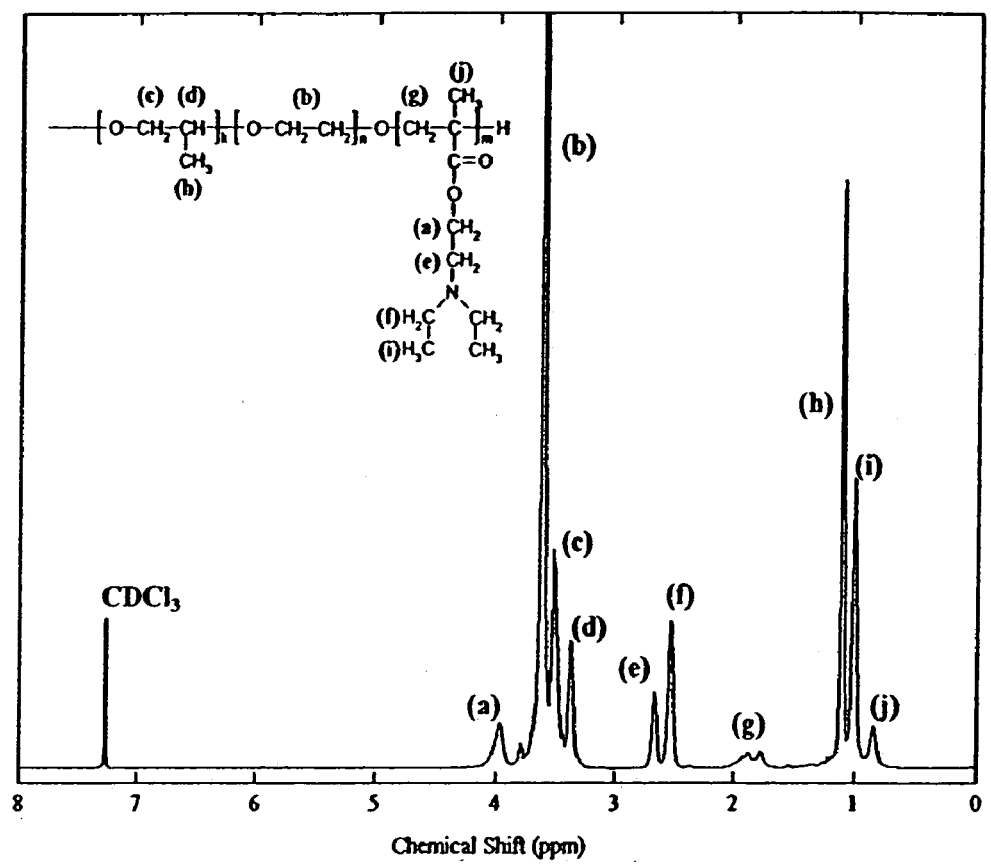
FIG. 6 is an $^1$H NMR analysis of PDEAEM-b-PEO-b-PPO-b-PEO-b-PDEAEM.

A sample NMR of a pentablock material with peak assignments is given as FIG. 6 (integration of peaks (a), (b), (c), (d), (e) and (f) were used in $\overline{M}_n$ calculations). The $\overline{M}_n$ values for the DEAEM blocks can cover a wide range, however our release studies focused on a specific range of molecular weight. Simple dissolution and gelation tests indicated the pentablock material A (Table 1) appeared to be in a molecular weight range and DEAEM/initiator ratio that produced interesting pH-sensitive behavior while maintaining the desirable properties of F127. As a result, material A was used for the bulk of the release studies. It should be recognized, however, that materials with customized DEAEM block lengths and mass fractions can easily be prepared by the addition of slightly more or less of the cationic moiety.

Gel Permeation Chromatography

Target molecular weights, estimated actual molecular weights, PDI and percent DEAEM of the Example 2 pentablock copolymers are set forth in Table 1 below. The relative amount of PDEAEM is reported as percent mass of the methacrylate blocks relative to the total weight of the copolymer. NMR values were used for $\overline{M}_n$, and the PDI was approximated from GPC.

Gel Permeation Chromatography (GPC) was used to obtain the polydispersity index of the pentablock copolymer. THF was used as the mobile phase with a sample injection volume of 100 µl. The system was equipped with three PLgel columns (Polymer Laboratories, Amherst, Mass.) heated to 40° C. An Optilab inline refractive index detector (Wyatt Corp, Santa Barbara, Calif.) was used as the detector for retention times of the synthesized polymers relative to poly(methyl methacrylate) and polystyrene standards.

Differential scanning calorimetry was performed on the pentablock copolymer using a DSC7 (Perkin Elmer, Shelton, Conn.) to measure the critical micellization temperature. Samples were cooled to −10° C. and held at this temperature for 15 minutes before beginning a temperature scan from −10° C. to 35° C. at a rate of 5° C./min under a nitrogen purge. The critical micellization temperature was determined as the onset of the deviation of the endothermic micellization transition peak from the baseline.

Values for $\Delta H$, $T_m$ and $\Delta S$ are given for 28% w/w aqueous samples over a wide range of PDEAEM block lengths in Table 2. Samples at lower polymer concentrations are also reported for the 36.2% DEAEM pentablock copolymer and the Pluronic® triblock copolymer. Samples denoted by a "*" contained 2.8% NBCl dye and 25.2% polymer. Numbers in parentheses are the sample standard errors for the measurements.

TABLE 2

Thermodynamic properties of polymer gels obtained from pentablock materials.

| Sample ID | % Polymer | % DEAEM | $T_m$ (° C.) | $\Delta H$ (J/g) | $\Delta S$ (J/gK) |
|---|---|---|---|---|---|
| B | 28% | 19.6% | −0.73 (4.19) | 4.38 (0.79) | 16.1 (3.16) |
| C | 28% | 9.3% | 0.18 (0.64) | 5.55 (0.38) | 20.3 (1.38) |
| D | 28% | 5.4% | 1.90 (0.65) | 5.17 (0.17) | 19.3 (0.57) |
| E | 28% | 1.9% | 2.12 (1.00) | 5.32 (0.79) | 18.8 (0.27) |
| H | 28% | 0% | 2.61 (0.10) | 6.01 (0.19) | 21.8 (0.69) |
| A | 27% | 36.2% | 1.92 (2.15) | 3.56 (0.30) | 13.0 (1.19) |
| H* | 25.2% | 0% | 9.00 (0.28) | 5.28 (0.52) | 18.7 (1.83) |
| A* | 25.2% | 36.2% | 7.83 (0.36) | 3.35 (0.68) | 11.9 (2.43) |

The trend seen in the data presented in Table 2 indicates that the addition of the PDEAEM blocks slightly depresses $T_m$ and reduces the magnitude of the endothermic $\Delta H$. The magnitude of this depression is not great for the smaller PDEAEM block lengths, namely 10% and less, however the magnitude increases for the larger PDEAEM block lengths. Although the trend is clear, a Tukey multiple comparison test ($\alpha$=0.05) indicated that only the extreme samples, 0%–36.2% and 0%–20%, were statistically significant for $\Delta H$ and $\Delta S$. For $T_m$, all samples were statistically the same at a 0.05 level due to the large variance in measured values. However, the values for samples H* and A* are a good example of the $T_m$ and $\Delta H$ depression. The differences between these samples, as seen in a t-test for different means, are statistically significant to a p<0.01 level for both $T_m$ and $\Delta H$.

The reason for the $\Delta H$ depression is an apparent reduction in the entropic driving force for micellization. The PPO core of the micelles is the influential factor for micellization. It is assumed that the PDEAEM portions of the pentablock material partitioned into the hydrophobic micelle core due to the fact PDEAEM is quite hydrophobic and would at least be partially solvated by the PPO nanophase. This would lead to a reduction in entropic advantage to micellization, and thus the observed change in enthalpy and entropy of micellization. In addition, limited hydrogen bonding with the methacrylate at temperatures below the CMT may have partially disrupted the hydrophobic effect, the entropic driving force for micellization. The depression in $T_m$ with increasing PDEAEM block length was most likely due to an increase in the amount of hydrophobic characteristic of the polymer. It was observed that more monomeric units of hydrophobic species, the lower the micellization temperature.

For pentablock materials terminated with benzyl bromide, the phenyl peaks were integrated relative to the known PEG Pluronic® peaks at ~3.7 ppm to determine the average number of benzyl termini per molecule. The terminal signals integrated against the PEG peak divided by the number of equivalent PEG protons in the initiator showed a ratio of 10:1, or two benzyl groups per Pluronic® initiator molecule. This indicated that according to the procedure, we were able to prepare materials that were fully pentablock in nature. Whether the block lengths were identical could not be verified, however the benzyl termination procedure allowed some insight into the material's molecular structure.

pH-Sensitivity

Release studies were performed using the pentablock copolymer to determine its effectiveness in drug delivery. Nile blue chloride dye (NBCl) Nile blue chloride (NBCl) (Sigma-Aldrich) with a visible absorbance maximum at 636 nm, MW=375.0) was used as the model drug due to its moderate water solubility, and molecular weight of 375.0 g/mol, and because it made a suitable model drug for many small molecules that do not partition exclusively into lipophilic or aqueous phases. The absorbance maxima of NBCl in the visible spectra at 636 nm also made release rates easy to measure without interference from the dissolved polymer.

Dissolution of the pentablock copolymer samples was tested using a 10:1 polymer to dye solution prepared in ethanol. The ethanol was evaporated leaving a homogeneous polymer/dye solid. Cold aqueous solutions were then prepared from this material using the method described by Anderson, et al., *Journal of Controlled Release*, 70:157 (2001). The samples were then placed in appropriate containers, typically glass dishes with a radius of 14 mm and height of 10 mm, and placed in a 37° C. oven, where they formed non-crosslinked hydrogels.

Figure 7:
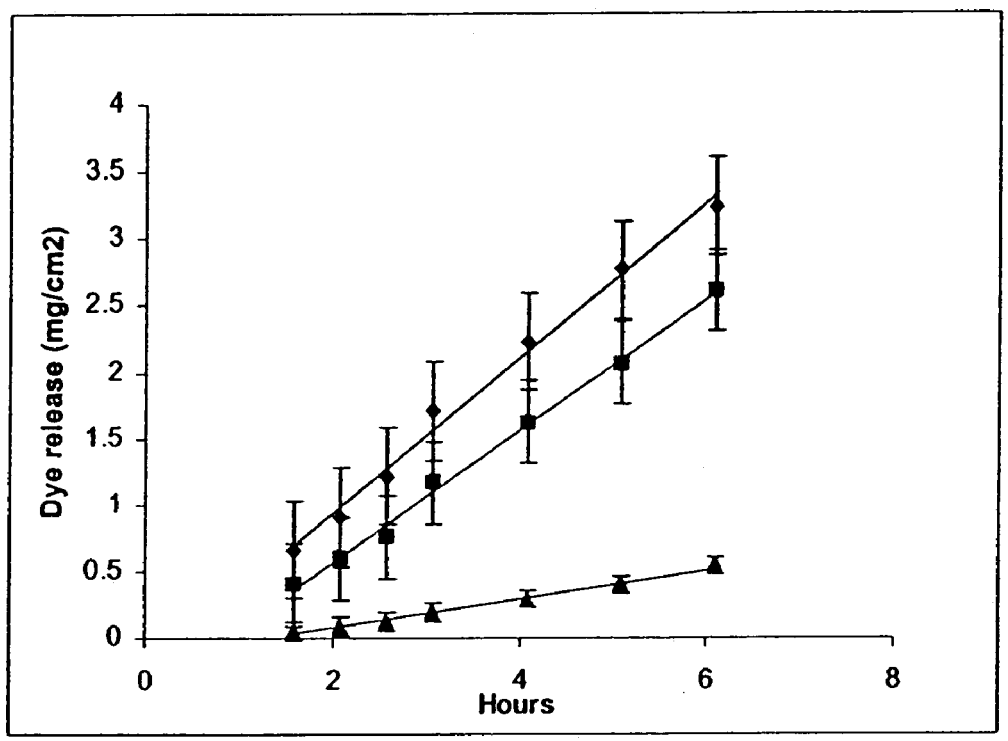
FIG. 7 illustrates the release rate of Nile blue chloride from PDEAEM-b-PEO-b-PPO-b-PEO-b-PDEAEM pentablock copolymer gels, sample A, as a function of pH

The tablet dissolution studies of the pentablock materials revealed a pH sensitivity in 28% w/w pentablock copolymer gels. Once the material set into a non-crosslinked gel, the release of molecules was dependent on the pH of the buffer (FIG. 7). As described in previous work for Pluronic® systems, protons were carried into the interfacial area of the gel as water penetrated the gel. Typically when crosslinked membranes containing PDEAEM become protonated, they swell due to electrostatic interactions of the charged cations.

The same is true in the non-crosslinked case, however swelling leads to dissolution of the gel and release of the entrapped molecules.

The hydrogel samples were tested for pH sensitivity in a stirred dissolution tank at 37° C. with 800 ml of buffer solution (prepared by adding sodium phosphate to an appropriate amount of anhydrous monobasic sodium phosphate ($NaH_2PO_4$) and anhydrous dibasic sodium phosphate ($Na_2HPO_4$) to deionized water; 0.5M total ionic strength), and allowed to dissolve over a period of time. The samples were removed from the dissolution tanks at various intervals and tested for dye concentration using visible wavelength spectrophotometry. The agitation rate used was 60 RPM with a 10:1 F127:NBCl solution as a control. Release from Pluronic® gels served as a control. Poly(ethylene glycol) with $\overline{M}_n$ values of 5000 g/mol and 8000 g/mol were used as non-ionic controls and were used as received from Sigma-Aldrich (St. Louis, Mo.).

At the higher pH values, the gel was relatively insoluble. In lower pH buffers, the gel was soluble with a rate of dye release more than five times the rate at higher pH values. The release rates were computed from the slope of the release plots in FIG. 7. Again the non-ionic control material, the Pluronic®, proved to be pH-insensitive in its release profile, and had a release rate similar to the pentablock copolymer at low pH values. The release from Pluronic® F127 gels occurred at a rate of 0.57 mg/cm²/hour for a loading of 30 mg/cm³. A lack-of-fit test for this data indicated a p-value of 0.54 from an F-statistic value of 0.898.

Cytotoxicity Testing

Elution tests were performed on one sample of the pentablock material to assess the cytotoxic properties of the pentablock copolymers. Approximately 30 mg of the polymers to be tested were dissolved in 100 ml of low-glucose Dulbecco's modified eagle medium (DMEM, Sigma) with 10% fetal bovine serum (FBS, Sigma), 10 μg/ml insulin (Sigma), 10 units/ml penicillin/streptomycin (Sigma), and 100 μg/ml L-ascorbic acid (Sigma). This solution was diluted to achieve the desired polymer concentration for all tests.

NIH/3T3 mouse fibroblasts were grown in polystyrene flasks until reaching confluence at 150 cells/mm. The growth media was removed from the flasks and replaced with one of the following: DMEM (negative control), DMEM with phenol (positive control), DMEM with the pentablock material. The concentrations of the pentablock material and phenol were 3 mg/L, 0.3 mg/L and 0.03 mg/L.

After 24 hours of incubation in a humidified incubator with 5% $CO_2$ at 37° C. the samples were removed and the media was replaced with Karnovsky's fixative (2.5% glutaraldehyde, 2.0% paraformaldehyde, 0.1M sodium cacodylate) for 12 hours. The samples were then stained with a 20% crystal violet dye (CVD) solution in ethanol for 6 hours followed by dehydration with ethanol. The cell layer was then inspected for a cytotoxic response by noting changes in cell density, morphology and adherence relative to the positive and negative control samples.

The results of the tests were compared to a negative control and a positive control. The negative control, pure growth media, was taken as the result expected for a non-cytotoxic material. The positive control, phenol laced media, was taken as the result expected for a cytotoxic material. The pentablock material, at the same concentration as the phenol positive control, led to results similar to the negative control. The fibroblast cells used in the tests showed good adhesion to the polystyrene cell culture substrate and the cells remained confluent after the 24 hour test period, neither of which is true for the positive control.

Structural Characteristics

Figure 8:
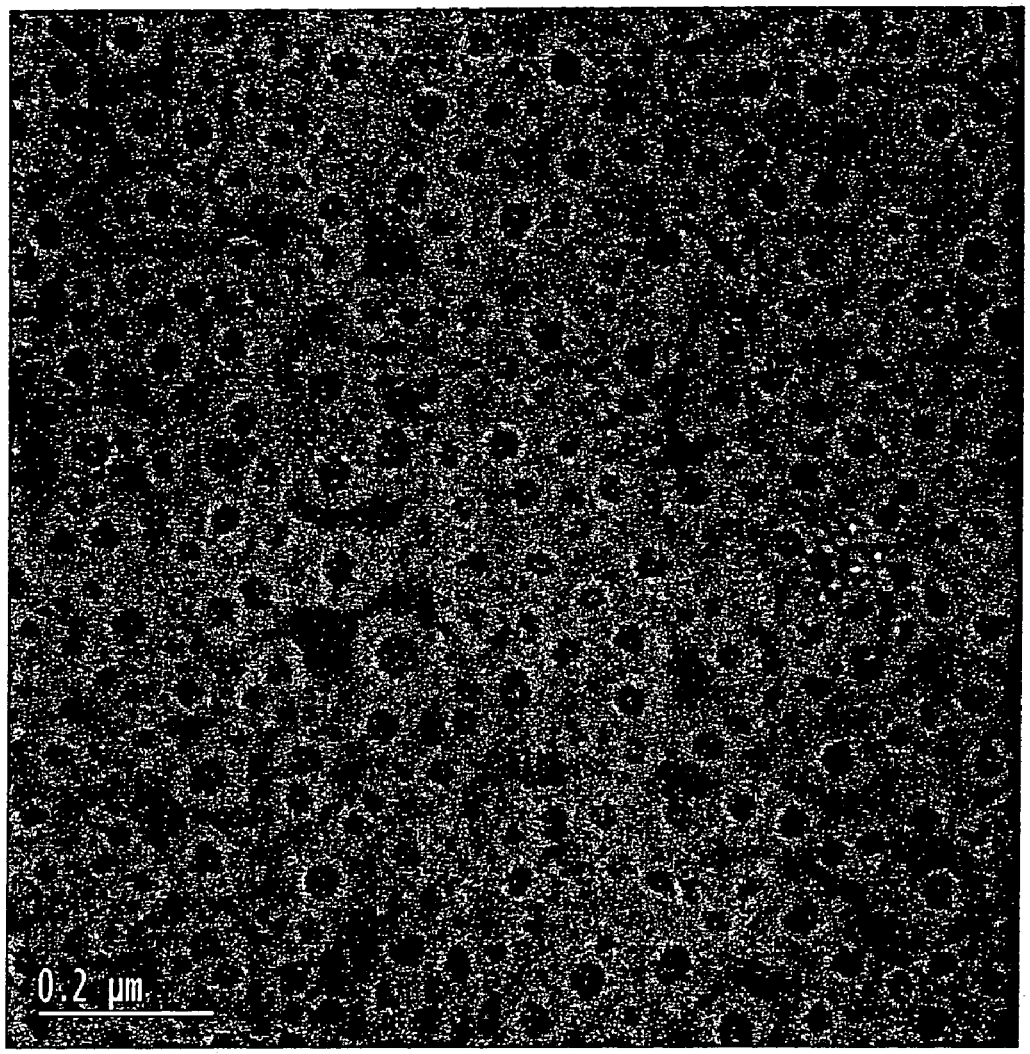
FIG. 8 is photograph showing the pentablock copolymers in the form of nanoscale in solution.
Figure 9:
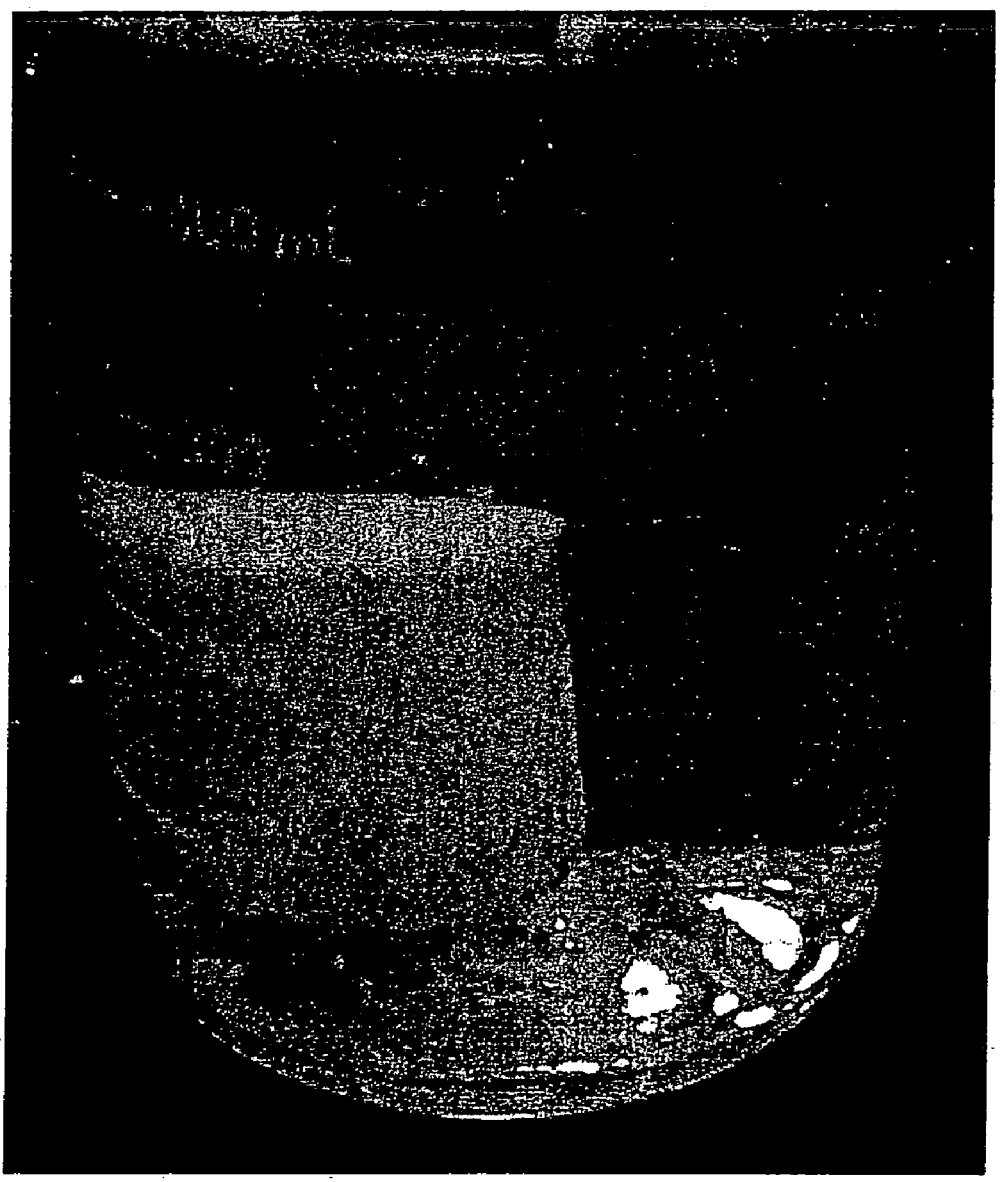
FIG. 9 is a photograph of a solid pentablock copolymer having 36%–37% by weight PDEAEM.

The pentablock copolymers were analyzed for their structural characteristics. As illustrated in FIG. 8, pentablock copolymers having a DEAEM concentration by weight of about 17% are maintained in an aqueous solution when at temperatures below 37° C. As illustrated in FIG. 9, at 37° C. and neutral pH, the aqueous solution of copolymers transitions into a gel. At about 70–80° C. and at basic pH (pH of greater than 10), the copolymers further condense by self assembly to form blobs.

Figure 10:
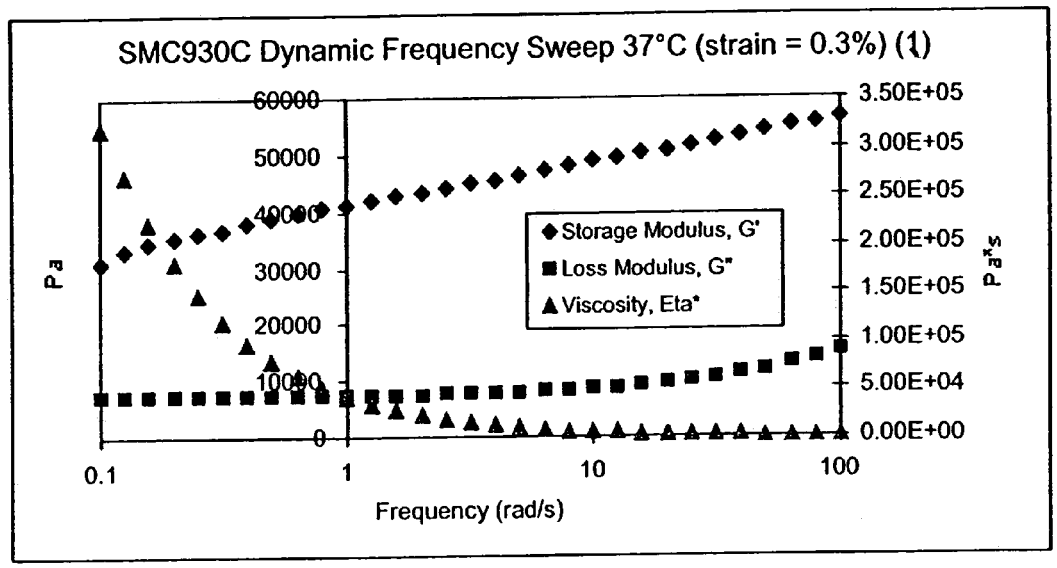
FIG. 10 is a graph illustrating results from a dynamic frequency sweep of the solid pentablock copolymer having 36%–37% by weight PDEAEM.

Slices of solid pentablock copolymer gels having 36–37% PDEAEM by weight were cut and mechanically tested using dynamic mechanical analysis to show that the materials exhibit a solid behavior. Strain and frequency sweeps were carried out using SMC930C to measure the elastic and viscous moduli of the materials. Our results (FIG. 10) indicated that the materials possessed elastic and viscous moduli characteristics having a order of magnitude similar to that expected for native nucleus pulposus as reported by Iatridis et al., *Spine,* 21(10):1174 (1996).

We claim:

1. An injectible bodily prosthetic having a structural supplement comprising a copolymer in aqueous solution, the solution forming a gel at or above a physiological temperature selected from the group consisting of 35° C. and 37° C., the solution being at a temperature below the physiological temperature, the copolymer being represented by the following formula (I):

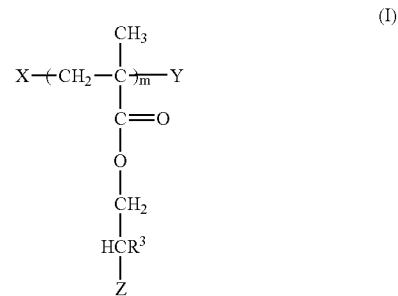

wherein m is an integer in the range of 1 to 5000, X is

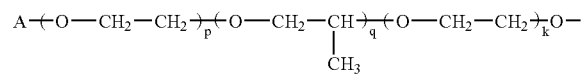

wherein p is an integer in the range of 30 to 20,000, q is an integer in the range of 1 to 20,000, and k is an integer in the range of 0 to 20,000, and A is

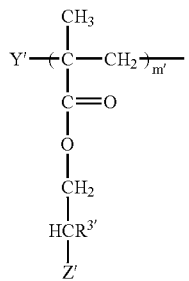

wherein m' is an integer in the range of 0 to 5,000;

Y and Y' are selected from the group consisting of X,

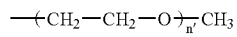

wherein n' is in the range of 30 to 20,000, and a terminator group;

$R^3$ and $R^{3'}$ are selected from the group consisting of a hydrogen and a $C_{1-6}$ alkyl group; and Z and Z' are selected from the group consisting of $NR^6R^7$, $P(OR^8)_3$, $SR^9$, SH,

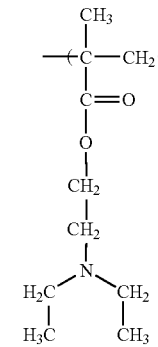

wherein $R^6$, $R^7$, and $R^8$ are the same or different $C_{1-6}$ alkyl groups, $R^9$ is a tri($C_{1-6}$ alkyl) silyl group, and B is a $C_{1-6}$ alkyl group.

2. The prosthetic of claim 1 wherein k is 0.
3. The prosthetic of claim 1 wherein k is a positive integer.
4. The prosthetic of claim 1 wherein m' is 0.
5. The prosthetic of claim 4 wherein Y' is a hydrogen.
6. The prosthetic of claim 1 wherein $R^3$ is a hydrogen.

7. The prosthetic of claim 1 wherein Y' is a terminator group.

8. The prosthetic of claim 7 wherein the terminator group is selected from the group consisting of a benzene, an alkyl group, a carboxylic group, COOH, $CH_2$—Ph, $CH_3$, and a hydrogen.

9. The prosthetic of claim 1 wherein Z' is $NR^6R^7$ and $R^6$ and $R^7$ are the same $C_{1-6}$ alkyl group.

10. The prosthetic of claim 1 wherein Z' and Z are the same.

11. The prosthetic of claim 1 wherein Y and Y' are the same.

12. The prosthetic of claim 11 wherein Y is a terminator group.

13. The prosthetic of claim 12 wherein the terminator group is selected from the group consisting of a benzene, an alkyl group, a carboxylic group, COOH, $CH_2$—Ph, $CH_3$, and a hydrogen.

14. The prosthetic of claim 1 wherein Y in formula (I) is

15. The prosthetic of claim 14 wherein $R^3$ is a hydrogen.
16. The prosthetic of claim 14 wherein Z is $NR^6R^7$ and $R^6$ and $R^7$ are the same $C_{1-6}$ alkyl group.
17. The prosthetic of claim 1 wherein the copolymer is

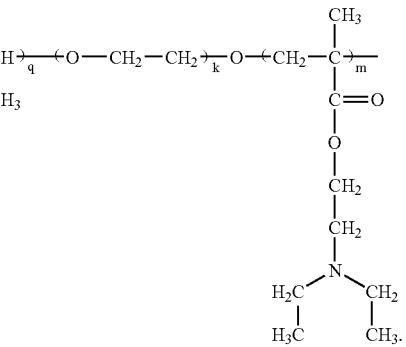

18. The prosthetic of claim 17 wherein k is 0.
19. The prosthetic of claim 17 wherein k is a positive integer.
20. The prosthetic of claim 17 wherein m' is 0.
21. A method for introducing a bodily prosthetic into a patient, the method comprising the steps of:

(a) injecting an aqueous solution of a copolymer into the patient at a location in which the bodily prosthetic is to be placed wherein the solution forms a gel at or above a physiological temperature selected from the group consisting of 35° C. and 37° C., the solution being at a temperature below the physiological temperature, the copolymer being represented by the following formula (I):

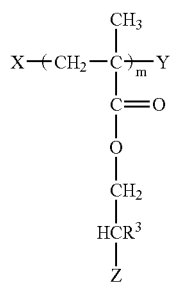
(I)

wherein m is an integer in the range of 1 to 5000, X is

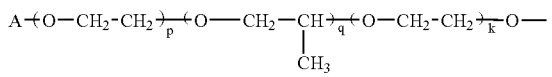

wherein p is an integer in the range of 30 to 20,000, q is an integer in the range of 1 to 20,000, and k is an integer in the range of 0 to 20,000, and A is

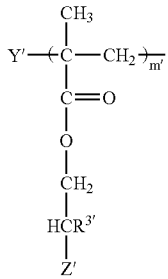

wherein m' is an integer in the range of 0 to 5,000; Y and Y' are selected from the group consisting of X,

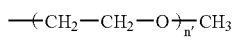

wherein n' is in the range of 30 to 20,000, and a terminator group;

$R^3$ and $R^{3'}$ are selected from the group consisting of a hydrogen and a $C_{1-6}$ alkyl group; and Z and Z' are selected from the group consisting of $NR^6R^7$, $P(OR^8)_3$, $SR^9$, SH,

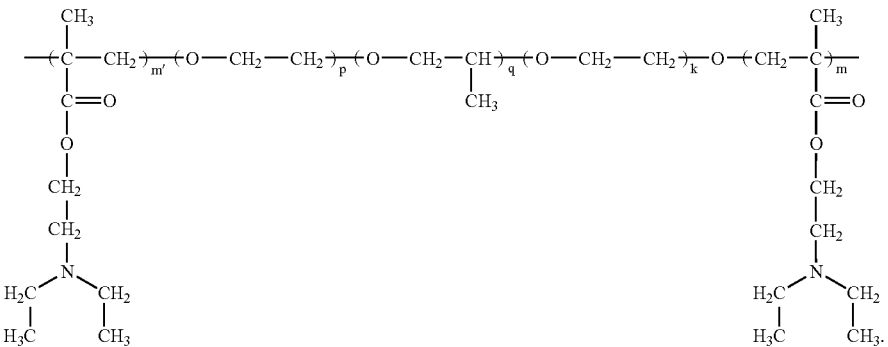

wherein $R^6$, $R^7$, and $R^8$ are the same or different $C_{1-6}$ alkyl groups, $R^9$ is a tri($C_{1-6}$ alkyl) silyl group, and B is a $C_{1-6}$ alkyl group; and (b) increasing the temperature of the solution so that the solution forms a gel.

22. The method of claim 21 wherein the copolymer is

23. The method of claim 22 wherein k is 0.
24. The method of claim 22 wherein k is a positive integer.
25. The method of claim 22 wherein m' is 0.
26. The method of claim 21 further comprising the step of injecting a basic solution into the patient at the location in which the bodily prosthetic is to be placed.
27. The method of claim 21 further comprising the step of injecting a crosslinking agent into the patient at the location in which the bodily prosthetic is to be placed.
28. The method of claim 27 wherein the crosslinking agent comprises a member selected from the group consisting of a diacid, a diamine, and an anhydride version of a diacid.
29. The method of claim 21 further comprising the step of injecting the copolymer into a synthetic membrane.
30. The method of claim 29 wherein the membrane is placed in the patient prior to the membrane being injected with the copolymer.
31. The method of claim 29 wherein the membrane is placed in the patient after the membrane is injected with the copolymer.
32. The method of claim 21 wherein the prosthetic is placed in between the vertebrae of the patient or in a body part selected from the group consisting of buttocks, face breasts, legs, and joints.

33. The method of claim 32 wherein the prosthetic is placed in between the vertebrae.

34. The method of claim 33 wherein the prosthetic replaces a nucleus pulposus.

35. A method of replacing the nucleus pulposus of a patient, the method comprising the steps of:

(a) injecting an aqueous solution of a copolymer in between the vertebrae of a patient wherein the solution forms a gel at or above a physiological temperature selected from the group consisting of 35° C. and 37° C., the solution being at a temperature below the physiological temperature, the copolymer being represented by the following formula (I):

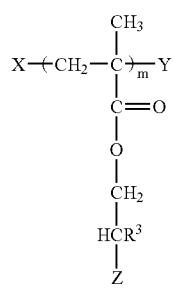
(I)

wherein m is an integer in the range of 1 to 5000, X is

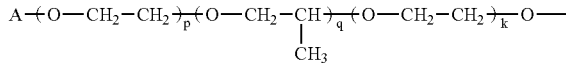

wherein p is an integer in the range of 30 to 20,000, q is an integer in the range of 1 to 20,000, and k is an integer in the range of 0 to 20,000, and A is

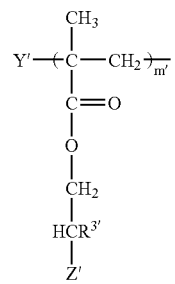

wherein m' is an integer in the range of 0 to 5,000,
Y and Y' are selected from the group consisting of X,

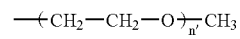

wherein n' is in the range of 30 to 20,000, and a terminator group;
$R^3$ and $R^{3'}$ are selected from the group consisting of a hydrogen and a $C_{1-6}$ alkyl group; and
Z and Z' are selected from the group consisting of $NR^6R^7$, $P(OR^8)_3$, $SR^9$, SH,

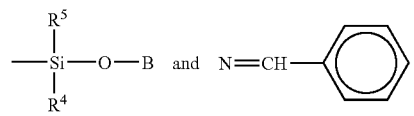

wherein $R^6$, $R^7$, and $R^8$ are the same or different $C_{1-6}$ alkyl groups, $R^9$ is a tri($C_{1-6}$ alkyl) silyl group, and B is a $C_{1-6}$ alkyl group; and (b) increasing the temperature of the solution so that the solution forms a gel.

36. The method of claim 35 wherein the copolymer is

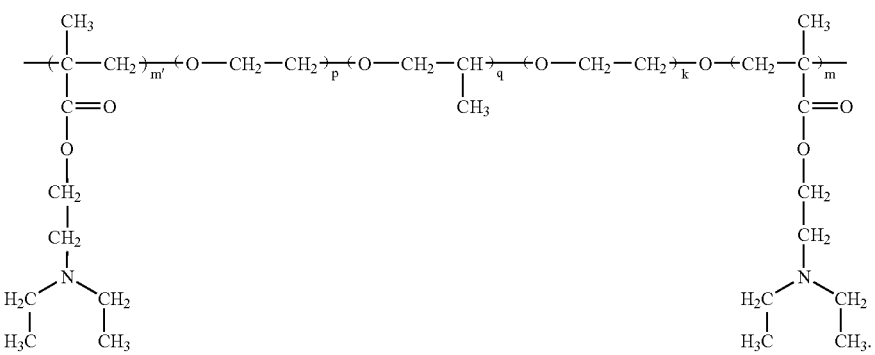

37. The method of claim 35 further comprising the step of injecting a basic solution into the vertebrae of the patient such that the copolymer reacts with the basic solution.

38. The method of claim 35 further comprising the step of injecting a crosslinking agent into the patient such that the copolymer reacts with the crosslinking agent.

39. The method of claim 38 wherein the crosslinking agent comprises a member selected from the group consisting of a diacid, a diamine, and an anhydride version of a diacid.

* * * * *